(12) United States Patent
Danehy et al.

(10) Patent No.: US 10,385,383 B2
(45) Date of Patent: Aug. 20, 2019

(54) SYSTEMS AND METHODS FOR BIOLOGICAL ANALYSIS

(71) Applicant: LIFE TECHNOLOGIES CORPORATION, Carlsbad, CA (US)

(72) Inventors: Ronald Danehy, Shirley, MA (US); Gary Lim, San Francisco, CA (US); Jacob Freudenthal, San Jose, CA (US)

(73) Assignee: Life Technologies Corporation, Carlsbad, CA (US)

( * ) Notice: Subject to any disclaimer, the term of this patent is extended or adjusted under 35 U.S.C. 154(b) by 304 days.

(21) Appl. No.: 15/048,324

(22) Filed: Feb. 19, 2016

(65) Prior Publication Data

US 2016/0168626 A1    Jun. 16, 2016

Related U.S. Application Data

(62) Division of application No. 14/348,881, filed as application No. PCT/US2012/058042 on Sep. 28, 2012, now Pat. No. 9,267,170.

(Continued)

(51) Int. Cl.
*C12Q 1/6806* (2018.01)
*C12M 1/32* (2006.01)
(Continued)

(52) U.S. Cl.
CPC ........ *C12Q 1/6806* (2013.01); *B01L 3/50851* (2013.01); *B01L 3/50855* (2013.01); *B01L 3/50857* (2013.01); *C12M 23/12* (2013.01); *C12M 23/38* (2013.01); *B01L 2200/026* (2013.01); *B01L 2200/0642* (2013.01);
(Continued)

(58) Field of Classification Search
CPC .................. B01L 3/50255; B01L 3/5088
See application file for complete search history.

(56) References Cited

U.S. PATENT DOCUMENTS

| 4,798,706 A | 1/1989 | Brigati |
| 5,979,251 A | 11/1999 | James et al. |

(Continued)

FOREIGN PATENT DOCUMENTS

| CN | 201535776 U | 7/2010 |
| CN | 201581079 U | 9/2010 |

(Continued)

OTHER PUBLICATIONS

Search Report in Application No. 11201401911X, dated Apr. 20, 2015.

(Continued)

*Primary Examiner* — Matthew D Krcha

(57) ABSTRACT

A case for containing a plurality of biological samples contains a base, a substrate and a cover. The substrate is attached to the base and comprises a plurality of reaction regions configured to receive one or more biological samples. The cover comprises an inner surface and is configured to be attached to the base such that the base and cover together provide a cavity containing the substrate. The inner surface includes a central area and a recessed area disposed about the central area. The central area is configured to cover the reaction regions, while the recessed area is offset from the central area in a direction normal to the inner surface.

18 Claims, 10 Drawing Sheets

Related U.S. Application Data

(60) Provisional application No. 61/541,366, filed on Sep. 30, 2011.

(51) Int. Cl.
*C12M 1/00* (2006.01)
*B01L 3/00* (2006.01)

(52) U.S. Cl.
CPC . *B01L 2200/0684* (2013.01); *B01L 2200/142* (2013.01); *B01L 2300/0819* (2013.01); *B01L 2300/0829* (2013.01); *B01L 2300/0858* (2013.01); *B01L 2300/0893* (2013.01); *B01L 2300/161* (2013.01)

(56) References Cited

U.S. PATENT DOCUMENTS

| | | | |
|---|---|---|---|
| 6,027,873 A | 2/2000 | Schellenberger et al. | |
| 6,171,780 B1* | 1/2001 | Pham | B01L 3/5085 422/552 |
| 2003/0072681 A1* | 4/2003 | Freudenthal | B01L 3/5025 422/501 |
| 2004/0018615 A1 | 1/2004 | Garyantes | |
| 2004/0171166 A1* | 9/2004 | Hunter | B01F 13/0071 436/164 |
| 2004/0208792 A1 | 10/2004 | Linton et al. | |
| 2005/0030615 A1 | 2/2005 | Mei et al. | |
| 2005/0260745 A1* | 11/2005 | Domansky | B01L 3/50255 435/294.1 |
| 2007/0140912 A1 | 6/2007 | Minot | |
| 2007/0166199 A1* | 7/2007 | Zhou | B01L 3/5025 422/400 |
| 2008/0175757 A1 | 7/2008 | Powell | |
| 2011/0152108 A1 | 6/2011 | Brenan et al. | |

FOREIGN PATENT DOCUMENTS

| | | | |
|---|---|---|---|
| EP | 1300462 | 4/2003 | |
| EP | 1333286 A1 | 8/2003 | |
| EP | 1860060 A1 | 11/2007 | |
| WO | WO-2009111696 A1 * | 9/2009 | B01L 3/50851 |

OTHER PUBLICATIONS

First Office Action with Search Report in Application No. CN201280059386.2, dated May 4, 2015.
Partial Search Report in Application No. PCT/US2012/058042, dated Mar. 1, 2013.
International Search Report in Application No. PCT/US2012/058042, dated May 13, 2013.
Written Opinion in Application No. SG11201401911X, dated Mar. 29, 2016.

* cited by examiner

SYSTEMS AND METHODS FOR BIOLOGICAL ANALYSIS

CROSS-REFERENCE TO RELATED APPLICATIONS

This application is a division of U.S. application Ser. No. 14/348,881, filed Mar. 31, 2014, which is a 371 U.S. national phase of international application no. PCT/US2012/058042, filed Sep. 28, 2012, which claims the benefit of priority of U.S. provisional application Ser. No. 61/541,366, filed Sep. 30, 2011, which disclosures are incorporated herein by reference in its their entirety.

BACKGROUND OF THE INVENTION

Field of the Invention

The present invention relates generally to systems, devices, and methods for observing, testing, and/or analyzing one or more biological samples, and more specifically to systems, devices, and methods for observing, testing, and/or analyzing an array of biological samples.

Description of the Related Art

Optical systems for biological and biochemical reactions have been used to monitor, measure, and/or analyze such reactions in real time. Such systems are commonly used in sequencing, genotyping, polymerase chain reaction (PCR), and other biochemical reactions to monitor the progress and provide quantitative data. For example, an optical excitation beam may be used in real-time PCR (qPCR) reactions to illuminate hybridization probes or molecular beacons to provide fluorescent signals indicative of the amount of a target gene or other nucleotide sequence. Increasing demands to provide greater numbers of reactions per test or experiment have resulted in instruments that are able to conduct ever higher numbers of reactions simultaneously.

The increase in the number sample sites in a test or experiment has led to microtiter plates and other sample formats that provide ever smaller sample volumes. In addition, techniques such as digital PCR (dPCR) have increased the demand for smaller sample volumes that contain either zero or one target nucleotide sequence in all or the majority of a large number of test samples. There is a need for systems and sample format that will provide reliable data in a high-density sample format.

BRIEF DESCRIPTION OF THE DRAWINGS

Embodiments of the present invention may be better understood from the following detailed description when read in conjunction with the accompanying drawings. Such embodiments, which are for illustrative purposes only, depict novel and non-obvious aspects of the invention. The drawings include the following figures.

DETAILED DESCRIPTION OF THE DRAWINGS

Figure 1:
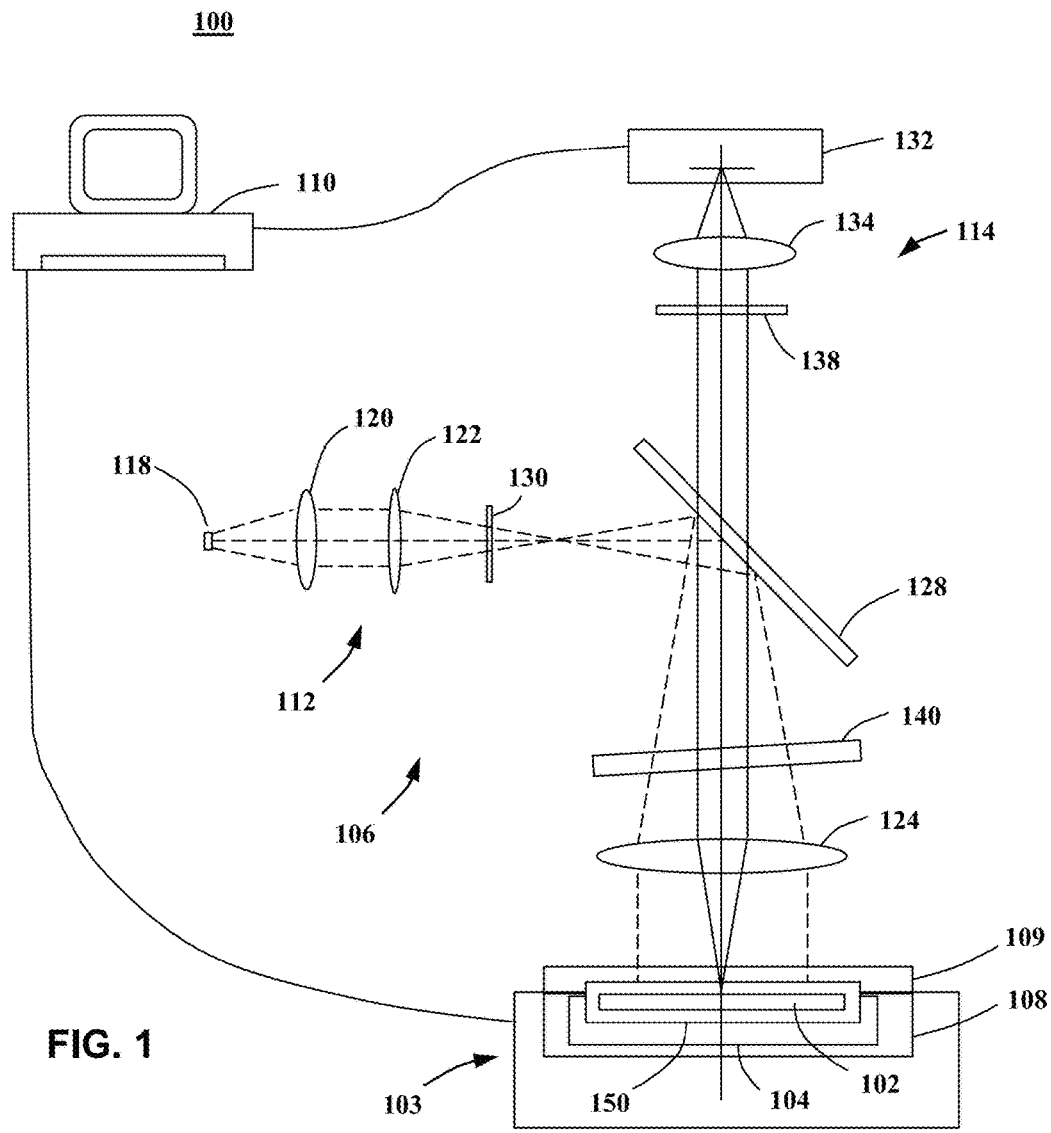
FIG. 1 is a system for processing a plurality of biological samples according to embodiments of the present invention.

Referring to FIG. 1, a system 100 for biological analysis comprises a sample holder, substrate, or plate 102 configured to hold a plurality of biological samples. In certain embodiments, system 100 may further comprise any or all of a carrier or support frame 104 for retaining, locating, and/or supporting sample holder 102, a base or mount 103 for receiving the sample holder 102, an optical system 106 for monitoring and/or measuring one or more biological processes of the biological samples, a thermal controller 108 for maintaining and/or cycling a thermal environment of the biological samples and/or sample holder 102, a heated lid 109 disposed above the sample holder for control of the environment about or within the biological samples and/or sample holder 102, and one or more electronic processors 110 with associated electronic memory and algorithms for controlling, monitoring, and/or measuring the one or more biological processes occurring in the biological samples. In various embodiments, system 100 comprises an instrument including a combination of some or all of carrier 104, base 103, optical system 106, thermal controller 108, heated lid 109, and/or one or more the electronic processors 110.

In certain embodiments, system 100 and sample holder 102 are suitable for performing real-time PCR processes on a plurality of biological samples. In other embodiments, system 100 and sample holder 102 are suitable for performing other biological or biochemistry processes such as sequencing or genotyping measurements. In the illustrated embodiment, optical system 106 comprises an excitation system 112 for illuminating sample holder 102 and the associated biological samples, and an emission optical system 114 for receiving emissions from the biological samples, for example, due to fluorescent signals produced by one or more fluorescent dyes or probe molecules present in the biological samples and in response to an excitation beam. Excitation optical system 112 includes an excitation source 118, lenses 120, 122, 124, beamsplitter 128. Excitation optical system 112 may also include one or more optical filters 130 for limiting the wavelength range of light received by the biological samples. Emission optical system 114 includes optical sensor 132, lenses 124, 134, beamsplitter 128. Emission optical system 114 may also include one or more optical filters 138 for limiting the wavelength range of light received by optical sensor 132. In addition, optical system 106 may include one or more windows 140 configured to isolate portions of system 100, for example, to reduce or eliminate unwanted thermal or optical effects during processing of the biological samples.

In certain embodiments, sample holder 102 is disposed within an enclosure, housing, or case 150 that may be sealed, for example, to reduce or prevent evaporation of the biological samples. In certain embodiments, one or more sample holders 102 or sample cases 150 are retained, located and/or supported by carrier 104 configured for aligning and/or transporting the sample holder 102 within system 100.

Figure 2:
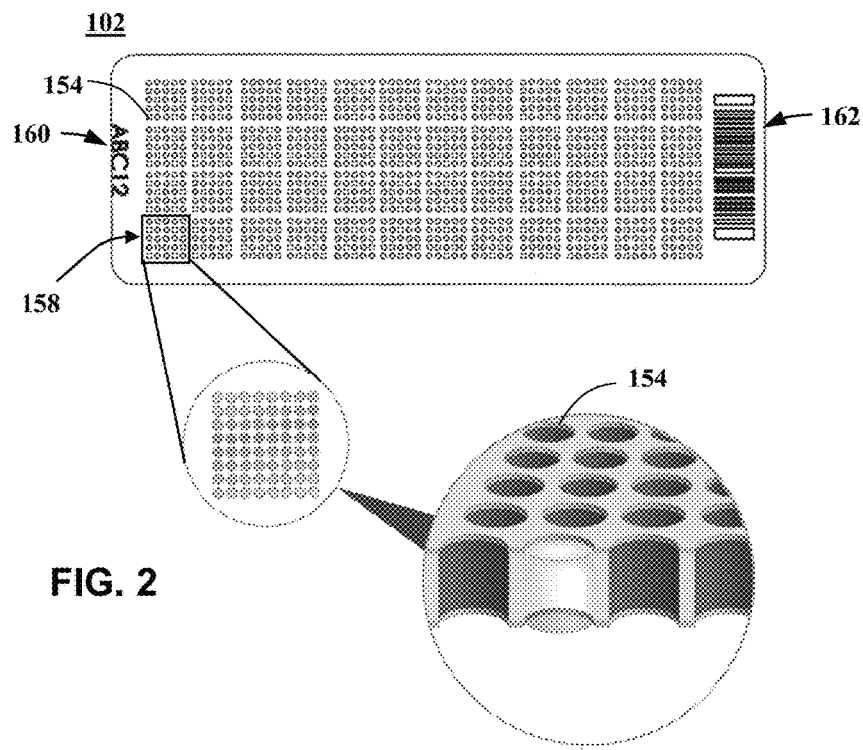
FIG. 2 is a sample holder according to an embodiment of the present invention comprising a plurality of through-holes.

Referring to FIG. 2, sample holder 102 may include a substrate comprising opposing surfaces and a plurality of reaction regions, wells, or vials 154 disposed over one or both surfaces. In the illustrated embodiment shown in FIG. 2, reaction regions 154 comprise a plurality of through-holes disposed between the opposing surfaces of sample holder 102. In certain embodiments, through-holes 154 are evenly spaced from one another along a two-dimensional array. Alternatively, through-holes 154 may be grouped in a plurality of subarrays 158, for example, to facilitate loading of samples into different groups of through-holes. For example, in the illustrated embodiment shown in FIG. 2, sample holder 102 comprises 4 by 12 subarrays, where each subarray comprises 8 by 8 individual through holes 154, for a total of 3072 through-holes 154 on sample holder 102. Through-holes 154 may be dimensioned such that a liquid containing a biological sample and/or reference dye is held within through-holes 154 by surface tension or capillary forces, as illustrated in the magnified view of FIG. 2. This effect may be enhanced by coating the walls of through-holes 154 with a hydrophilic coating. In certain embodiments, the outer surfaces of sample holder 102 comprise a hydrophobic material or coating configured to reduce or eliminate cross-contamination or mixing between the samples located in the various through-holes 154. Various aspects and advantages of a through-hole arrangement for supporting biological samples are further disclosed in U.S. Pat. Nos. 6,306,578; 6,893,877; 7,682,565, the entire contents of each of which patents are hereby incorporated by reference in their entirety for all purposes as if fully set forth herein.

In certain embodiments, an initial sample or solution for a sample holder, such as sample holder 102, may be divided into hundreds, thousands, tens of thousands, hundreds of thousands, or even millions of reaction sites, each having a volume of, for example, a few nanoliters, about one nanoliter, or less than one nanoliter (e.g., 10's or 100's of picoliters or less).

In the illustrated embodiment shown in FIG. 2, sample holder 102 has a rectangular shape; however, sample holder 102 may have other shapes, such as a square or circular shape. In certain embodiments, sample holder 102 has a square shape and an overall dimension of 15 millimeter by 15 millimeter. In such embodiments, sample holder 102 may have an active area, region, or zone with a dimension of 13 millimeter by 13 millimeter. As used herein, the terms "active area", "active region", or "active zone" mean a surface area, region, or zone of a sample holder, such as the sample holder 102, over which reaction regions, through-holes, or solution volumes are contained or distributed. In certain embodiments, the active area of sample holder 102 may be increased to 14 millimeter by 14 millimeter or larger, for example, a 15 millimeter by 15 millimeter substrate dimension.

In the illustrated embodiment of FIG. 2, through-holes 154 may have a characteristic diameter of 320 micrometer and a pitch of 500 micrometers between adjacent through-holes. In other embodiments, through-holes 154 have a characteristic diameter of 75 micrometer and have a pitch of 125 micrometers between adjacent through-holes. In yet other embodiments, through-holes 154 have a characteristic diameter of that is less than or equal 75 micrometers, for example, a characteristic diameter that is less or equal to 60 micrometers or less or equal to 50 micrometers. In other embodiments, through-holes 154 have a characteristic diameter that is less than or equal to 20 micrometers, less than or equal to 10 micrometers, or less than or equal to 1 micrometer. The pitch between through-holes may be less than or equal to 125 micrometers, for example, less than or equal to 100 micrometers, less than or equal to 30 micrometers, or less than or equal to 10 micrometers.

In certain embodiments, sample holder 102 comprises a substrate having a thickness between the opposing surfaces of sample holder 102 that is at or about 300 micrometer, wherein each through-hole 154 may have a volume of 1.3 nanoliter, 33 nanoliters, or somewhere between 1.3 nanoliter and 33 nanoliters. Alternatively, the volume of each through-holes 154 may be less than or equal to 1 nanoliter, for example, by decreasing the diameter of through-holes 154 and/or the thickness of sample holder 102 substrate. For example, each through-holes 154 may have a volume that is less than or equal to 1 nanoliter, less than or equal to 100 picoliters, less than or equal to 30 picoliters, or less than or equal to 10 picoliters. In other embodiments, the volume some or all of the through-holes 154 is in a range from 1 nanoliter to 20 nanoliters.

In certain embodiments, the density of through-holes 154 is at least 100 through-holes per square millimeter. Higher densities are also anticipated. For example, a density of through-holes 154 may be greater than or equal to 150 through-holes per square millimeter, greater than or equal to 200 through-holes per square millimeter, greater than or equal to 500 through-holes per square millimeter, greater than or equal to 1,000 through-holes per square millimeter, or greater than or equal to 10,000 through-holes per square millimeter.

Advantageously, all the through-holes 154 with an active area may be simultaneously imaged and analyzed by an optical system. In certain embodiments, active area comprises over 12,000 through-holes 154. In other embodiments, active area comprises at least 25,000, at least 30,000, at least 100,000, or at least 1,000,000 through-holes.

In certain embodiments, through-holes 154 comprise a first plurality of the through-holes characterized by a first characteristic diameter, thickness, or volume and a second plurality of the through-holes characterized by a second characteristic diameter, thickness, or volume that is different than the first characteristic diameter, thickness, or volume. Such variation in through-hole size or dimension may be used, for example, to simultaneously analyze two or more different nucleotide sequences that may have different concentrations. Additionally or alternatively, a variation in through-hole 104 size on a single substrate 102 may be used to increase the dynamic range of a process or experiment. For example, sample holder 102 may comprise two or more subarrays of through-holes 154, where each group is characterized by a diameter or thickness that is different a diameter or thickness of the through-holes 154 of the other or remaining group(s). Each group may be sized to provide a different dynamic range of number count of a target polynucleotide. The subarrays may be located on different parts of substrate 102 or may be interspersed so that two or more subarrays extend over the entire active area of sample holder 102 or over a common portion of active area of sample holder 102.

In certain embodiments, at least some of the through-holes 154 are tapered or chamfered over all or a portion of their walls. The use of a chamfer and/or a tapered through-holes have been found to reduce the average distance or total area between adjacent through-holes 154, without exceeding optical limitations for minimum spacing between solution sites or test samples. This results in a reduction in the amount liquid solution that is left behind on a surface of substrate 102 during a loading process. Thus, higher loading efficiency may be obtained, while still maintaining a larger effective spacing between adjacent solution sites or test samples for the optical system.

In the illustrated embodiment shown in FIG. 2, sample holder 102 may also comprise alphanumeric characters 160, a barcode 162, or other symbolic representations from which information relative to an individual holder 102 may be derived or ascertained. Such information includes, but is not limited to, reagents contained with some or all of the through-holes 154 and/or protocols to be followed when using sample holder 102. In certain embodiments, emission optical system 114 is configured so that optical sensor 132 may be used to read characters 160 and/or barcode 162. In addition, emission optical system 114 may be configured to provide images that contain, in a single frame, portions of sample holder 102 containing through-holes 154 and either, or both, alphanumeric characters 160 or a barcode 162. In some embodiments, emission optical system 114 is configured to provide images that contain, in a single frame, portions of two or more sample holders 102 containing through-holes 154 for each sample holder 102 and either, or both, alphanumeric characters 160 or a barcode 162 the same sample holders 102.

Figure 3:
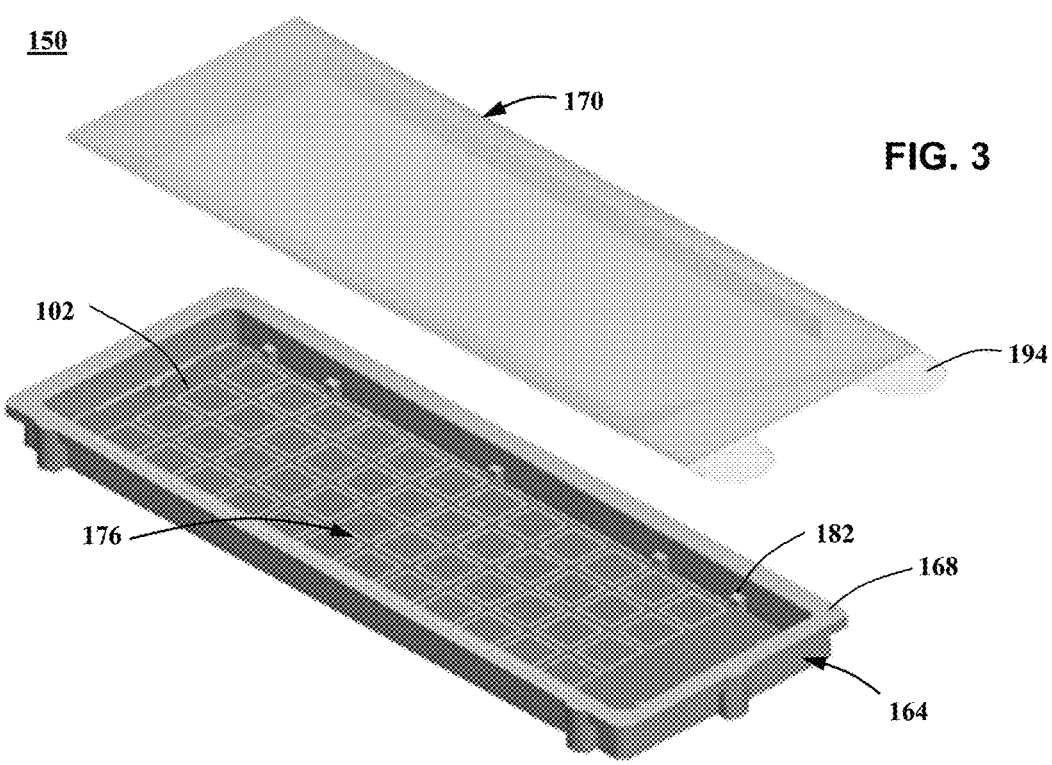
FIG. 3 is a perspective view of a case according to an embodiment of the present invention containing the sample holder shown in FIG. 2.
Figure 4:
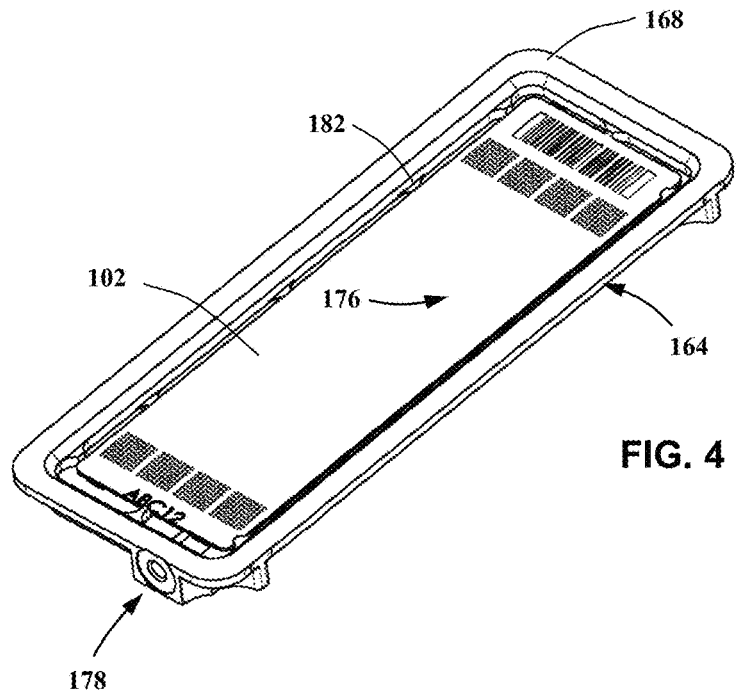
FIG. 4 is a perspective view of a base of the case according to an embodiment of the present invention containing the sample holder shown in FIG. 2.
Figure 5:
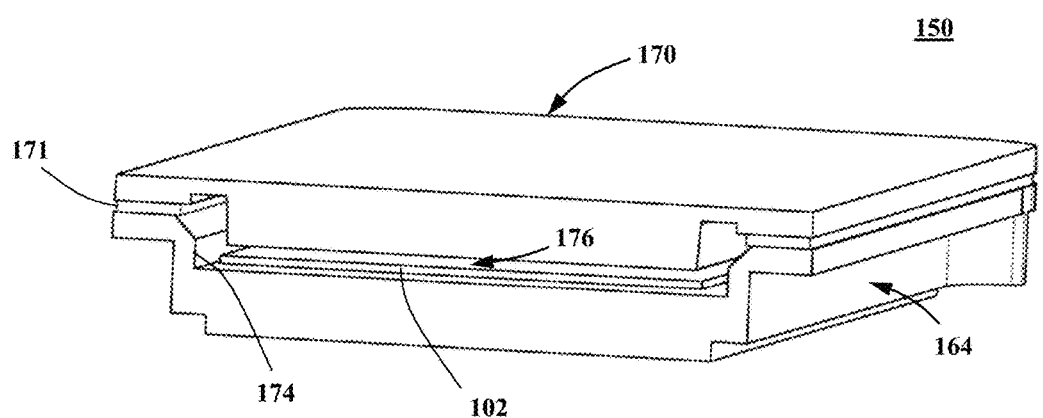
FIG. 5 is a cross-section view of a case according to an embodiment of the present invention showing a sample holder disposed between a base and a cover.

Referring to FIG. 3, in certain embodiments, case 150 comprises a base 164 having a top surface 168 and a cover 170 that sealably engages top surface 168 of base 164 to form an enclosure for containing sample plate 102 so as to at least partially isolate or separated the biological samples from an outside environment. Case 150 may also optionally comprise a gasket or seal 171 located between base 164 and cover 170. With further reference to FIGS. 4-8, base 164 comprises a bottom surface 172 and side walls 174 that, together with cover 170, form a cavity, chamber, or enclosure 176 with sufficient depth to contain sample plate 102 completely inside cavity 176 and entirely below top surface 168 and cover 170, as illustrated in FIG. 5. Base 164 may further comprise one or more fill ports 178 for injecting fluid into cavity 176 after cover 170 is attached to base 164. Bottom surface 172 may comprise a completely or generally flat surface. Alternatively, bottom surface 172 may include one or more indentations 180. For example, in the illustrated embodiment shown in FIG. 5, indentation 180 is located proximal to fill port 178 and is configured to provide an enlarged working volume for allowing fluid to enter and air to exit as cavity 176 is filled with a liquid using a pipette or similar device.

In certain embodiments, the sealed case 150 is injected through fill port 178 with a sealing fluid or liquid that is hydrophobic in nature, which favorably seals, but does not mix with, biological samples that are more hydrophilic. The use of such a sealing fluid or liquid into case 150 may be used to further seal the biological samples within through-holes 154 and reduce or eliminate evaporation of the biological sample during thermal cycling at high temperatures (e.g., upper temperatures from 90 to 100° C.). A suitable sealing fluid includes, but is not limited to, Fluorinert™ material FC-70 manufactured by 3M.

Base 164 may also comprise a plurality of bosses, tabs, staking sites, or support pads 182 located above and/or integral with bottom surface 172. Support pads 182 may be configured to engage and secure sample holder 102. Alternatively, some of the support pads 182 may be configured to simply contact or support sample holder 102 along its length, for example, to reduce or prevent warping or bending of sample holder 102. Support pads 182 may additionally be configured to maintain a predetermined spacing between the bottom surface of sample holder 102 and bottom surface 172 of base 164. The number of support pads 182 may be selected to maintain a predetermined flatness of sample holder 102 when engaged by some or all of support pads 182. In certain embodiments, some of support pads 182 engage sample plate 102 in a lateral direction (e.g., along a plane parallel to bottom surface 172), while the remaining support pads 182 are configured to contact sample plate 102 only along a bottom face of plate 102. In other embodiments, sample plate 102 is engaged by at least some of support pads 182 through the use of a tool or fixture to displace some of the material of a support pad 182 in a lateral direction. In other embodiments, engagement between plate 102 and at least some of the support pads 182 is provide by use of an adhesive, epoxy, or weld material disposed between sample plate 102 and support pads 182.

In certain embodiments, in addition to or in place of the plurality of support pads 182, base 164 comprises a one or more rails configured to receive a peripheral portion of sample holder 102. For example, a pair of rails may be disposed along opposite side walls 174. The rails may be disposed along the entire length of each side wall 174. Alternatively, the rails may be disposed along only a portion of each side wall 174. In addition, one or more support pads 182 may be included along the opposite side walls 174 and/or along other walls 174 of base 164.

Base 164 may be made of a material having a relatively high thermal conductivity and/or a high thermal diffusivity, for example, a material having a thermal conductivity of at least 50 to 200 $W \cdot m^{-1} \cdot K^{-1}$ and/or a thermal diffusivity of at least about $8 \times 10^{-5}$ $m^2 \cdot s^{-1}$. Suitable materials include, but are not limited to metallic materials such as aluminum, copper, silver, or gold, or a semimetal such as graphite. Use of such materials assist in providing a uniform temperature (low thermal non-uniformity or TNU) or predetermined temperature profile bottom surface 172 of base 164, which in turn provides an uniform or predetermined temperature profile over sample holder 102.

In certain embodiments, provision of a low TNU or predetermined temperature profile over sample holder 102 is further enhanced by locating the bottom surface of sample holder 102 close to bottom surface 172 of base 164, while simultaneously preventing contact between bottom surface 172 and sample holder 102 over the entire extent of sample holder 102. To meet these conditions, in certain embodiments, sample holder 102 is disposed a nominal distance of less than 300 micrometers from the bottom surface 172 of base 164. In other embodiments, the nominal distance is less than 250 micrometers, less than 200 micrometer, or less than 100 micrometers.

The contact between support pads 182 and sample holder 102 may produce hot spot on the holder when the thermal conductivity of the case or pad material is much higher than the thermal conductivity of the sealing fluid inside cavity 176 used to reduce evaporation of a biological test sample from through-holes 154. For example, the Fluorinert™ FC-70 material cited above has a thermal conductivity of 0.07 W·m$^{-1}$·K$^{-1}$, which is compared to a thermal conductivity of greater than 200 W·m$^{-1}$·K$^{-1}$ for common metals. In certain embodiments, the problem of hot spots is solved by configuring support pads 182 to have a total contact area with sample holder 102 that is low.

Figure 6:
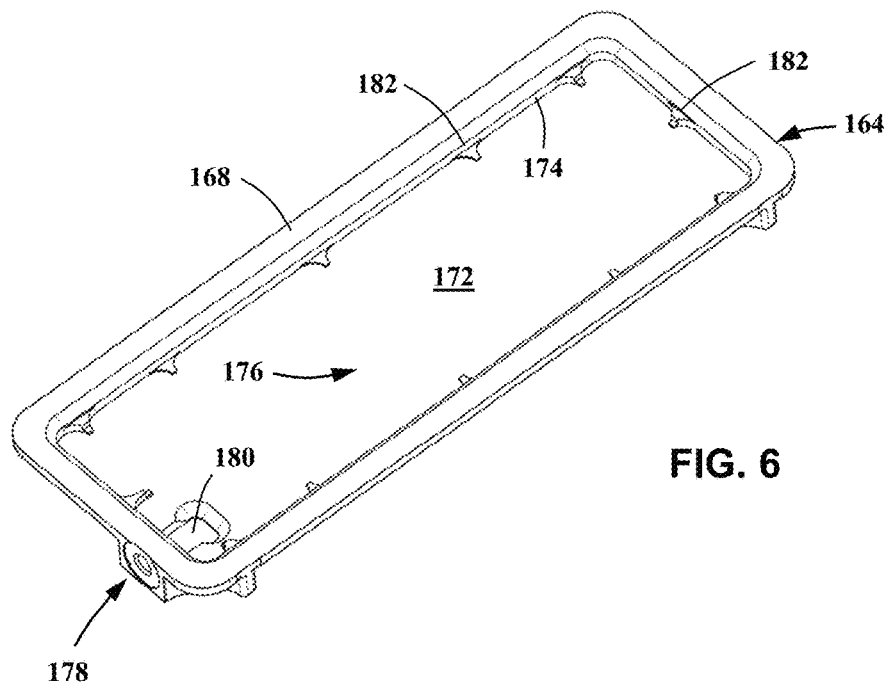
FIG. 6 is a perspective view the base shown in FIG. 4 without the sample holder.
Figure 7:
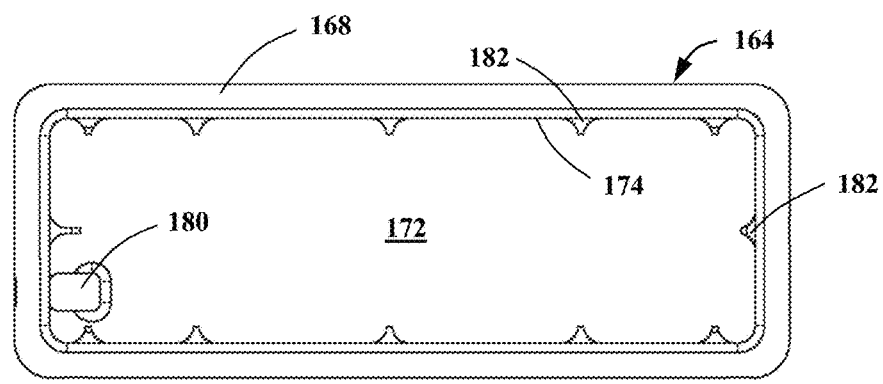
FIG. 7 is a top view of the base shown in FIG. 6.
Figure 8:
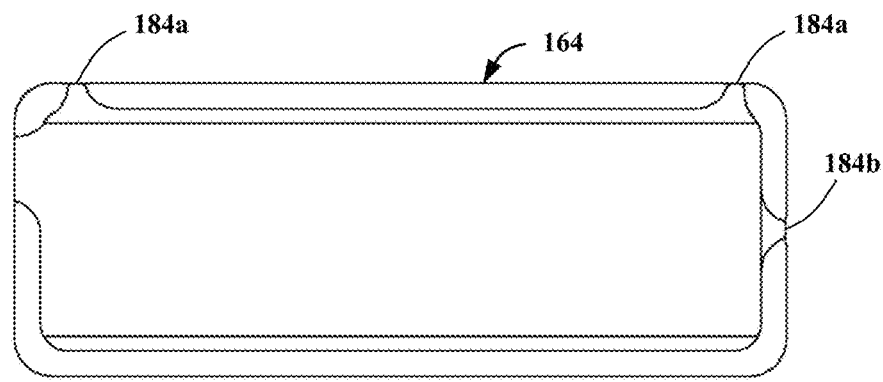
FIG. 8 is a bottom view of the base shown in FIG. 6.

A low total contact area may be achieve by providing a low number of support pads and by and by configuring individual pads to have a low contact area with sample holder 102. A lower bound on the number of support pads 182 is affected by the design constraint to maintain a low amount of bending or buckling of sample holder 102. In the illustrated embodiment, for example as seen in FIGS. 6 and 7, at least some of support pads 182 are tapered in a lateral direction; with a support pad 182 being relatively wide near side wall 174 and tapering off in width toward a tip of support pad 182. In this manner, the rigidity of support pads 182 is maintained, while the contact area with sample holder 102 is maintained at a low level that provide a low level of heat transfer into the hot spot.

In certain embodiments, sample holder 102 is secured or attached to base 164 prior to shipment to a customer, for example, to reduce or eliminate human contact with sample holder 102 during sample loading and use in system 100 by a customer or end user. In such embodiments, a tool or specialized fixture may be utilized so that a small amount of pad material is displaced laterally (e.g., along a plane parallel to bottom surface 172), where the laterally displaced material is in an amount sufficient secure, hold, or lock sample holder 102, but sufficiently small to eliminate bending or warping of sample holder 102. Alternatively, the amount of laterally displaced material is in an amount sufficient secure, hold, or lock sample holder 102 and to bend or warp sample holder 102 at or below a predetermined level.

In certain embodiments, an outer surface of base 164 comprise a plurality of registration features 184 to register and align case 150, sample holder 102, and/or through-holes 154 within system 100. For example, the two registration features 184*a* are used to align or register case 150 along an axis perpendicular to one of the long edges of sample holder 102, while registration feature 184*b* is used to align or register case 150 along an axis parallel to the long edges of sample holder 102.

Figure 9:
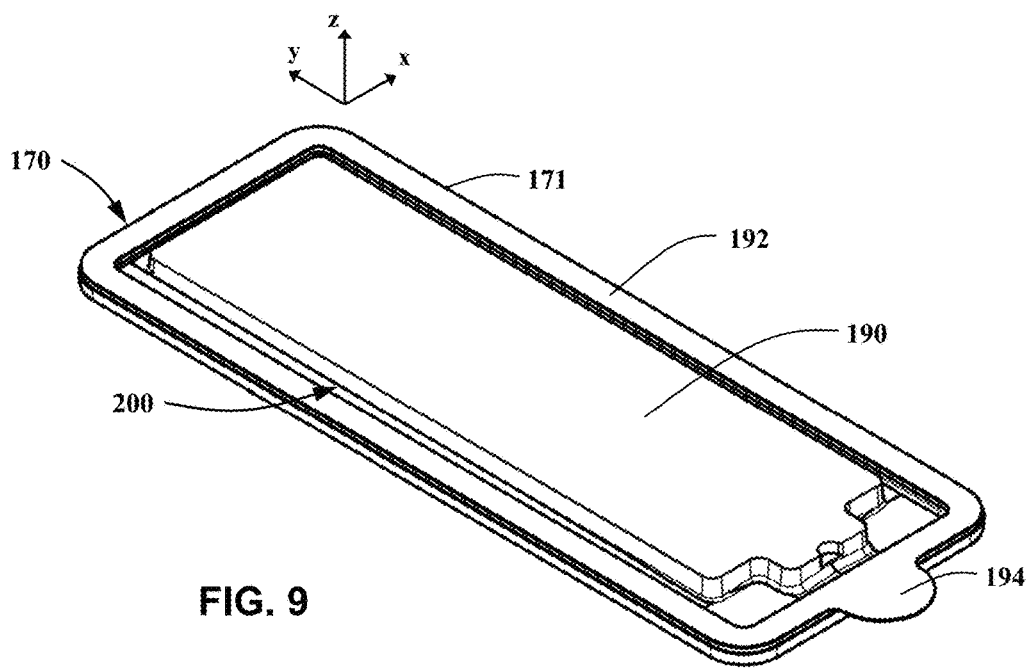
FIG. 9 is perspective view of the bottom of a cover according to an embodiment of the present invention.
Figure 10:
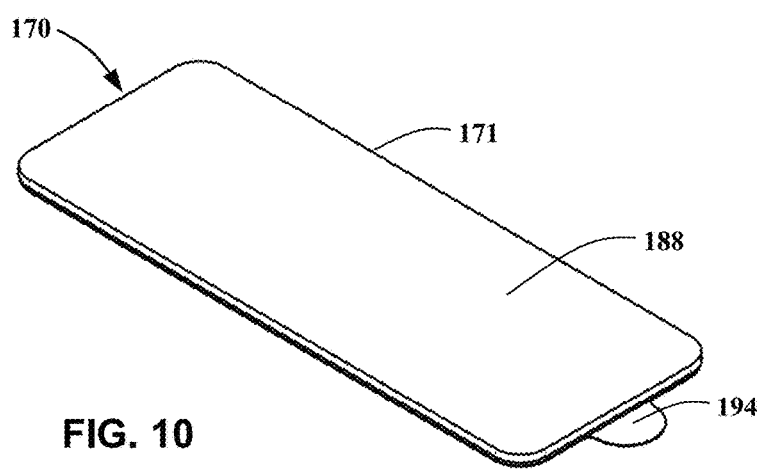
FIG. 10 is perspective view of the top of the cover shown in FIG. 9.

Referring to FIGS. 9-11, cover 170 comprises an outer surface 188 and an inner surface 190 including a rim 192 that interfaces with top surface 168 of base 164. At least portions of cover 170 comprise a transparent or relatively transparent in material to provide optical access to through-holes 154 and the biological or reference samples contained therein. Cover 170 may be made of a biocompatible material or another material if cover 170 is isolated from the biological samples contained in through-holes 154. Suitable materials for cover 170 include, but are not limited to, glass, acrylics, styrenes, polyethylenes, polycarbonates, and polyproplenes. In certain embodiments, the material comprises Cyclo Olefin Polymer (COP). In certain embodiments, cover 170 may include a lenslet array or diffractive optical element (not shown) configured to condition light being directed to or from through-holes 154. Cover 170 may be fabricated with seal 171 attached thereto. Alternatively, seal 171 is provided to a customer or user separate from cover 170, which are then attached to one another prior to use and application with base 164. Seal 171 may include an adhesive material on at least one surface for adhesion to base 164 and/or cover 170. Seal 170 may optionally include a removable non-stick layer 194 disposed over the adhesive material that is removed prior to use.

In certain embodiments, inner surface 190 comprises a surface profile, shape, or contour 200 that controls or manages bubbles in the sealing fluid discussed above that may from, for example, during processing of, or experimentation on, the biological samples contained in through-holes 154. Such embodiments take advantage of the natural tendency of bubbles to locate or move toward the top of a liquid media due to buoyancy. The introduction of bubbles into the sealing fluid may occur during the filling of cavity 176 with the sealing fluid or because of outgassing from the fluid itself, for example, during thermal cycling at high temperatures.

In certain embodiments, contour 200 and inner surface 190 comprise a central zone 210, peripheral zone 212, side zones 214, first end zone 220, and second end zone 222. Each zone may be further portioned. For example, in the illustrated embodiment shown in FIG. 11, first end zone 220 comprises a first area 230, a second area 232, and a third area 234. In discussing the shapes and locations of zones 210, 212, 214, 220, 222 and areas 230, 232, 234, a coordinate system will be adopted in which locations on inner surface 190 are more positive that locations on outer surface 188.

When assembled with the other components of case 150 and sample holder 102, central zone 210 is preferably suitable for optical inspection of, and located over, the plurality of through-holes 154 and any other features of sample holder 102 for which optical monitoring or inspection is desirable or required. For example, the central zone 210 may also extend over alphanumeric characters 160 and/or a barcode 162 so that they are available for optical inspection. Outer and inner surfaces 188, 190 within central zone 210 may be optically flat and parallel to one another. Alternatively, surfaces 188, 190 within central zone 210 may be optically flat and have a small offset angle relative to one another, for example, to reduce or eliminate multiple reflections between the surfaces, which reflections might reduce the image quality of data signals received by optical sensor 132. The offset angle between surfaces may be greater than or equal to 0.1 degrees and less than or equal to 0.5 degrees, 1 degree, 2 degrees, or 5 degrees, depending on the imaging specifications for system 100. In some embodiments, either or both surfaces 188, 190 may have an offset angle relative to a top surface of sample holder 102, for example an offset angle greater than or equal to 0.1 degrees and less than or equal to 0.5 degrees, 1 degree, 2 degrees, or 5 degrees, depending on the imaging specifications for system 100.

In the illustrated embodiment in FIG. 11, trough 250 has a bottom surface that is entirely below central zone 210 for the coordinate system shown in FIGS. 9 and 11B-11D, in which a positive direction along a normal to outer surface 188 (z-axis) is in a direction from outer surface 188 to inner surface 190. Thus, when case 150 is installed in system 100 with outer surface 188 above inner surface 190, any bubbles in cavity will tend to be located in trough 250 rather than in the area of central zone 210. In certain embodiments, trough 250 surrounds or encloses central zone 210 when viewed from below (e.g., as seen from the view in FIG. 11A); however, other configurations possible.

Figure 11A:
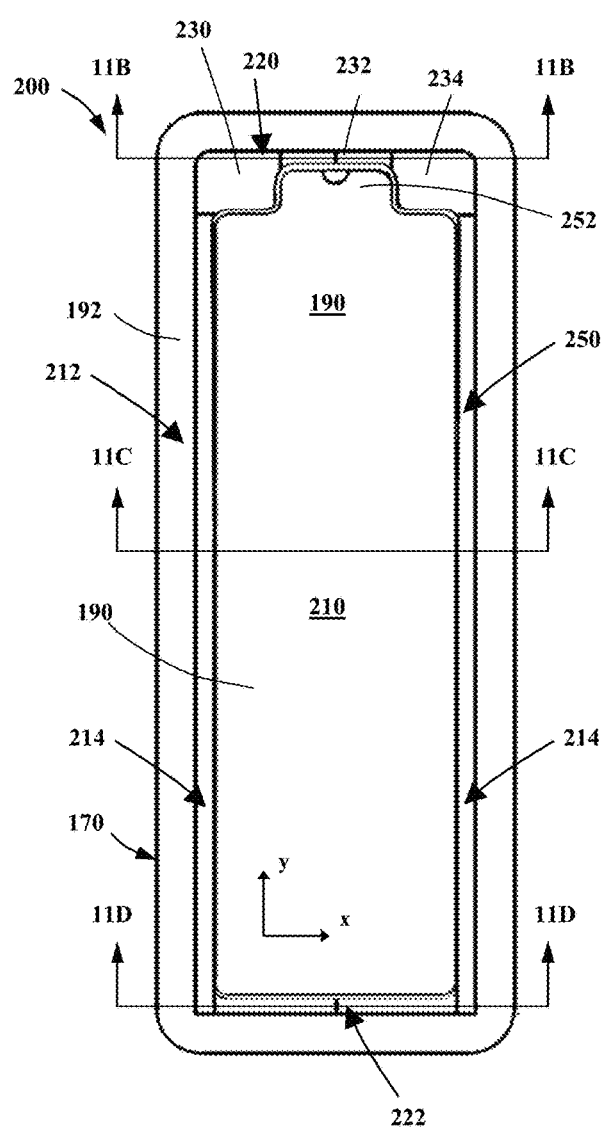
FIG. 11A is bottom view of cover shown in FIG. 9.

In certain embodiments, at least portions of central zone 210 are disposed at a minimum value, coordinate, or depth 240 and at least a portion of trough 250 is disposed at a maximum value, coordinate, or depth 242. In the illustrated embodiment, zones 212, 214, 222 form a channel, cannel, or trough 250. Trough 250 may have a constant depth along the entire trough. Alternatively, for example as shown in FIG. 11, trough 250 may have a bottom surface profile that varies in depth. For example, areas 230 and 234 of zone 220 have a depth equal to the minimum depth 240, while the remaining zones and areas of trough 250 have a depth that is less than the minimum depth. In such embodiments, any gas or bubbles in cavity 176 will tend to be located in areas 230, 234 in preference to the other zones of inner surface 190. As seen in FIG. 11A, end zone 220 may also be generally wider than other portions of trough 250 to further provide an enlarged area for the collection of bubbles or gas within the sealing fluid filling cavity 176, for example, to prevent first end zone 220 from filling with gas or bubbles, which could then spill over into unwanted portions of inner surface 190. In addition, enlargement of first end zone 220 may be advantageously configured maintain a relatively small overall size of case 150 while also providing a volume that is large enough to collect anticipated volumes of bubbles or entrapped gas. To aid in keeping the size of case 150 relatively small, central zone 210 includes a tabbed portion 252 that provides quality optical access to alphanumeric characters 160, which does not extend over the entire width of sample holder 102. Thus, areas 230, 234 of first end zone 220 have the enlarged width or volume compared to other portions of trough 250, while the width of area 232 is smaller and may be equal to or about equal to the width of other portions of trough 250.

Figure 11B:
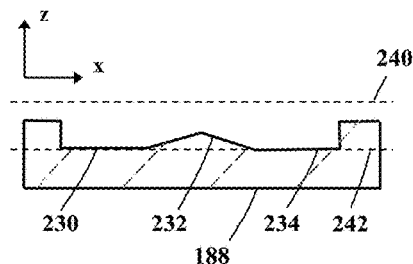
FIGS. 11B-11D are cross-sectional views of portions of the cover shown in FIG. 11A FIGS. 12A-12C are perspective views of a plug assembly according to an embodiment of the present invention.
Figure 11C:
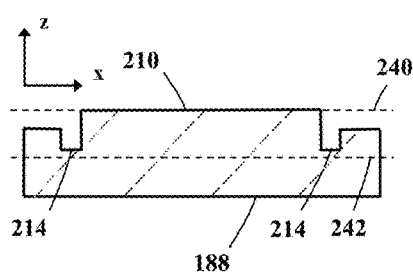
Figure 11D:
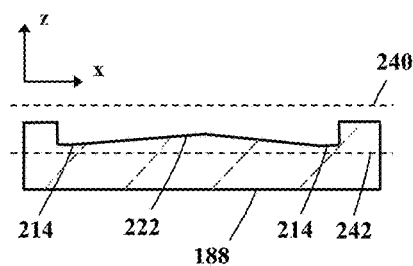

In certain embodiments, first end zone 220 may have a constant depth or substantially constant depth over its entire length. Alternatively, as in the illustrated embodiment shown in FIGS. 11A and 11B, areas 230, 234 of first end zone 220 may be separated by area 232, where area 232 has a depth that is less that either areas 230, 234. Areas 230, 234 may have the same depth or one of areas 230, 234 may have a depth that is less than the other; however, in such embodiments, area 232 has a depth that is less than the depth of areas 230, 234. The depth of area 232 may be constant or variable. For example, area 232 may have a profile that is sloped toward one of areas 230, 234 or is sloped toward both areas 230, 234, as illustrated in FIG. 11B. Second end zone 222 may have a constant depth or have a depth that is varied or sloped toward one of the side zones 214. Alternatively, second end zone may profile that is sloped toward both side zones 234, as illustrated in FIG. 11D. Both side zones 214 may have the same or different depth profiles compared to one another. In the illustrated embodiment, the depth of side zones 214 both less than the maximum depth of first end zone 220. All or a portion of each side zone 214 may have a depth that varies or slope along the channel formed thereby. For example, one or both side zones may be sloped from a minimum depth value at or near second end zone 222 and that increases to a maximum depth at or near first end zone 220.

Figure 12A:
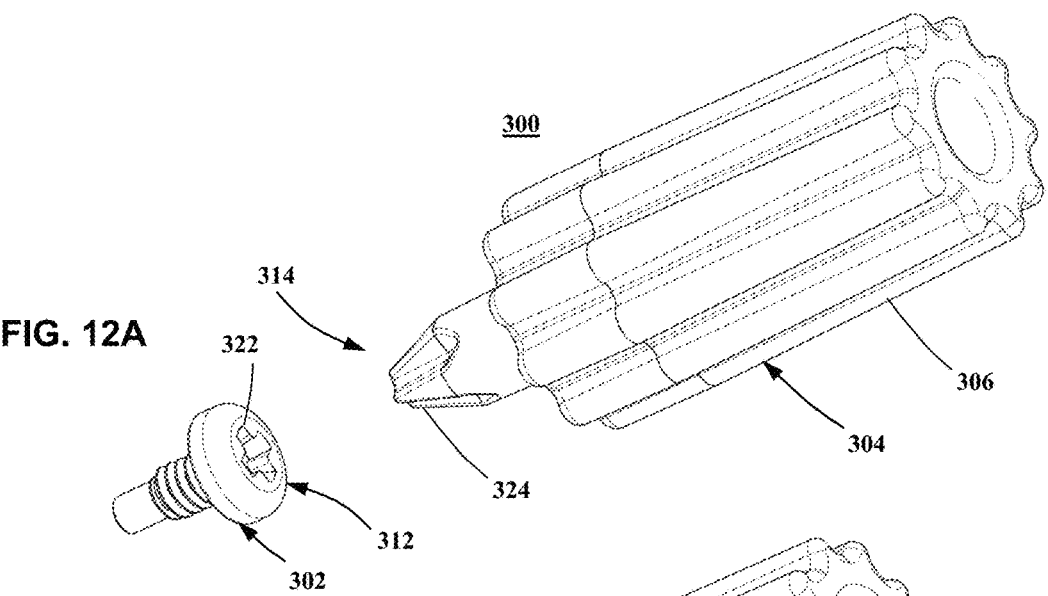
Figure 12B:
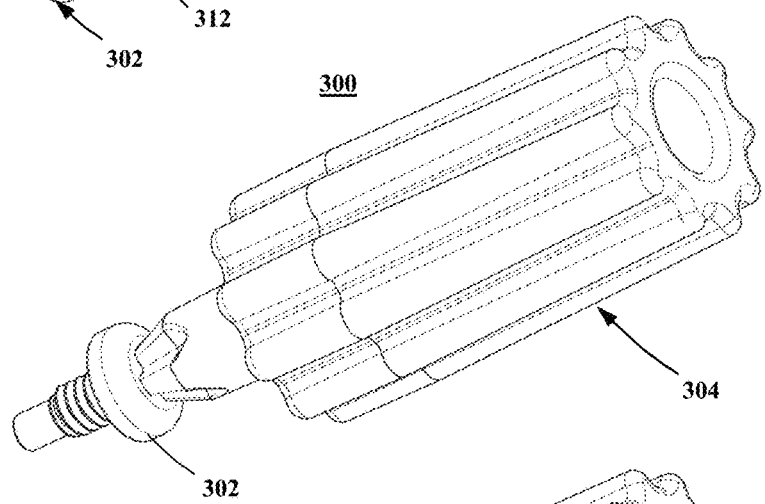
Figure 12C:
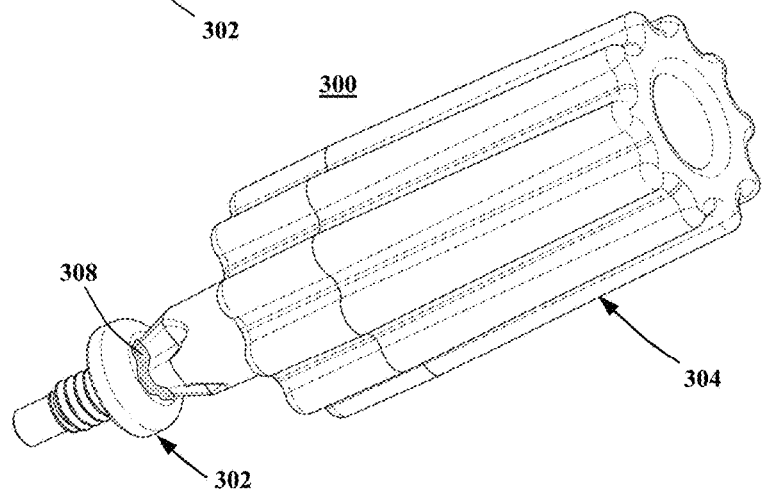
Figure 13:
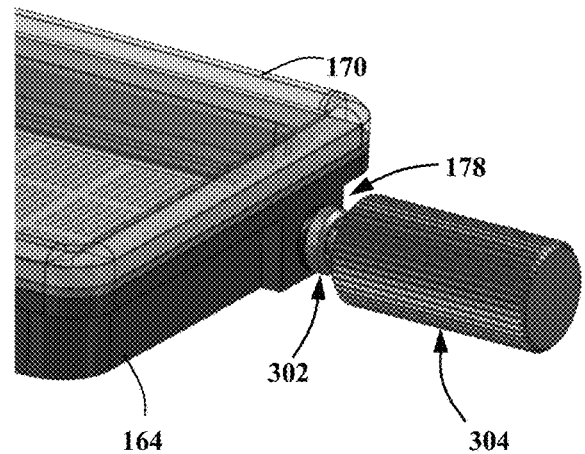
FIG. 13 is a perspective view a case according to an embodiment of the present invention showing attachment of the plug assembly shown in FIG. 12C.

Referring to FIGS. 12 and 13, in certain embodiment, case 150 includes a plug assembly 300 comprising a plug 302 and a plug driver 304 detachably coupled or joined to plug 302. Plug driver 304 is used to apply a driving force or torque to plug 302 as a means for sealing or plugging fill port 178 of case 150. As a means of providing a more compact unit, it is desirable in certain embodiments to separate plug driver 304 from plug 302 after insertion into fill port 178. To facilitate application of the driving force or torque, plug driver 304 may comprise a gnarled proximal end 306, for example, to allow direct hand application of the driving force or torque. Additionally or alternatively, the proximal end of plug driver 304 may comprise a configuration that allows tool or fixture to be applied for providing the desired driving force or torque.

Plug driver 304 may be coupled or attached to plug 302 using an epoxy 308, as illustrated in FIG. 12C. Alternatively, coupling or attachment of plug driver 304 to plug 302 may be providing using a glue or other type of adhesive, a solder joint, a weld joint, or the like. Plug 302 comprises a proximal end 312 having a first pattern 322, while plug driver 304 comprise a distal end 314 having a second pattern or form 324. First and second patterns 322, 324 complement one another in a way allow the patterns to be joined in a way allowing a force or torque to applied to plug driver 304 for driving plug 302 in order to plug or seal fill port 178 of case 150. In the illustrated embodiment, first pattern 322 has the form of a Phillips head screw, while second pattern 324 has the form of the tip portion of a Phillips head screw driver. Alternatively, first pattern 322 may have the form of the tip portion of a Phillips head screwdriver, while second pattern 324 may have the form of a Phillips head screw. Other types of standard bolt or screw head patterns may alternatively be used including, but not limited to, slot, socket, hex socket, hex head, one way screw head, spanner head, Trox, and the like. Alternatively, patterns 322, 324 may be a custom pattern and its complement.

In certain embodiment, the joint between plug driver 304 and plug 302 is sufficiently strong that a driving force or torque may be applied to plug driver 304 that is sufficient to plug or seal fill port 178 of case 150. Generally, the joint between plug driver 304 and plug 302 is sufficiently strong that the driving force or torque does not break or does not damage the joint and/or patterns 322, 324. In addition to these characteristics, the joint between driver 304 and plug 302 is sufficiently weak so that separating or breaking force or torque may be applied that breaks, separates, or decouples the joint between plug driver 304 and plug 302 in a manner that does not disturb or damage the seal produced at fill port 178 using the driving force or torque. In certain embodiments, the separating force or torque is only a little greater that the driving force or torque. For example, the separating force or torque may be less than or equal to 120% of the driving force or torque, less than or equal to 150% of the driving force or torque, less than or equal to 200% of the driving force or torque, or less than or equal to 400% of the driving force or torque. In certain embodiments, the separating force or torque is of a different type, or in a different direction, than the driving force or torque. For example, in the illustrated embodiment, plug 302 includes a threaded distal end that is screwed into fill port 178 using a driving torque about an elongate axis passing through both plug 302 and plug driver 304. Once plug 302 has been secured into fill port 178, a separating torque may be applied about a different axis, for example about an axis that is normal to the elongate axis. Alternatively or additionally, a lateral force perpendicular to the elongate axis may be applied to plug driver 304 as a separating force.

Figure 14:
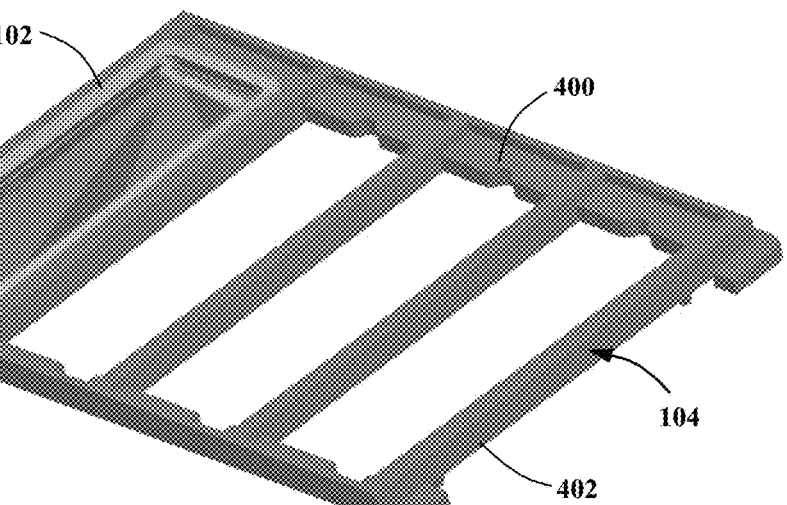
FIG. 14 is a perspective view of the top of a carrier according to an embodiment of the present invention and containing the case shown in FIG. 5
Figure 15:
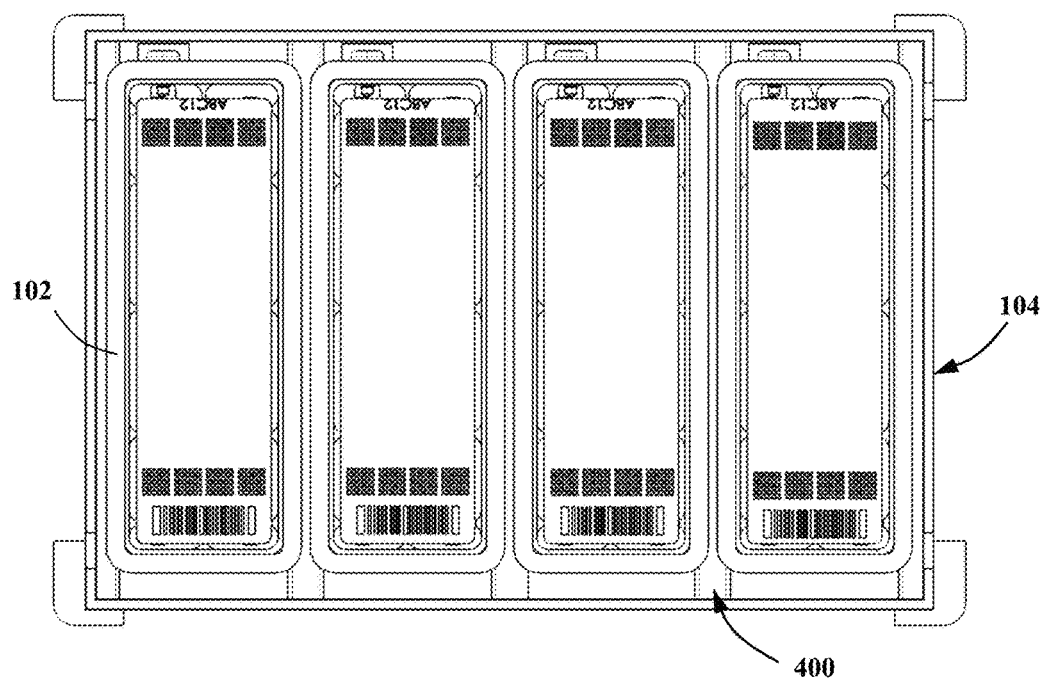
FIG. 15 is top view of the carrier shown in FIG. 14 and containing four of the bases and sample holders shown in FIG. 4.

Referring to FIGS. 14-15, carrier 104 may be configured support or hold a plurality of sample holders 102, for example, the four sample holders 102 shown in FIG. 15. Carrier 104 comprises a proximal or top side 400 that is configured to accommodate each of four separate sample holders 102 and a distal or bottom side 402 that is configured to interface or engage thermal controller 108 and/or configured to interface or engage each sample holder 102 with engage thermal controller 108. System 100 may be configured to accommodate one, two, three, or four sample holders using the same carrier in each case. For example, system 100 may include one or more sensors configured to sense how many sample holders 102 are present on or in carrier 104, and then make appropriate adjustment to test protocols for processing the biological samples, optical system configuration or performance, image processing algorithms, data presentation algorithms, and/or other mechanical, electrical, thermal, or optical elements or subsystems of system 100.

In certain embodiments, system 100 includes a one or more carrier configured to hold more or less than four sample holders 102. In other embodiments, system 100 includes one or more additional carriers configured to hold other types of sample holders. For example, system 100 may include additional sample holders configured to accommodate formats to hold 48, 96, and/or 384 individual samples. In such embodiments, a different carrier may be provided for each sample holder format, wherein each carrier comprise a first portion (e.g., a bottom side) that is the same or nearly the same as that of carrier 104, but wherein each carrier also comprises a second portion (e.g., a top side) having a different construction to accommodate each of the different types of sample holders.

Figure 16:
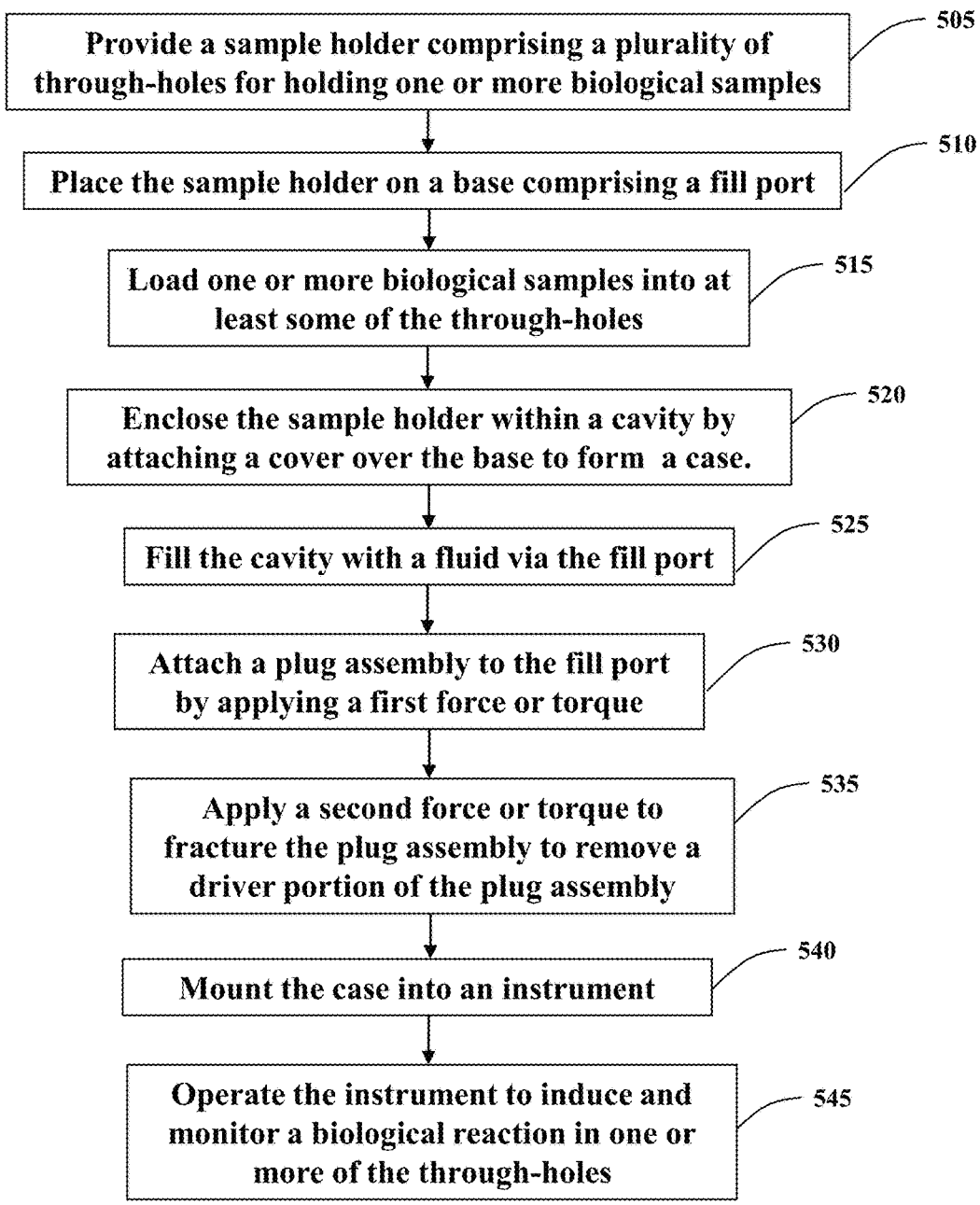
FIG. 16 is a flow chart of a method according to the present invention.

Referring to FIG. 16, in certain embodiments, a method 500 includes an element 505 comprising providing sample holder 102. Method 500 also includes an element 510 comprising locating, placing, or mounting sample holder 102 on or within base 164. Method 500 further includes an element 515 comprising loading one or more biological samples into at least some of through-holes 154. Method 500 additionally includes an element 520 comprising enclosing sample holder 102 within cavity 176 by attaching cover 170 onto or over base 164. Method 500 also includes an element 525 comprising filling cavity 176 with a fluid via fill port 178. Method 500 further includes an element 530 comprising attaching plug assembly 300 to the fill port 178 by applying a first force or torque. Method 500 additionally includes an element 535 comprising applying a second force or torque to fracture, part, or break plug assembly 300 and thereafter removing plug driver 304 from plug assembly 300. Method 500 also includes an element 540 comprising mounting case 150—including base 164, sample holder 102, and cover 170—into instrument 100. Method 500 further includes an element 545 comprising operating the instrument to induce and monitor a biological reaction in one or more of through-holes 154.

Regarding element 510 of method 500, sample holder 102 may be located on support pads 182 such that a bottom surface 172 of sample holder 102 is parallel or substantially parallel to bottom surface 172 of base 164. At least some of the support pads 182 may comprise a proximal portion having a top surface and attached to and/or integral with one of the side walls 174, and a distal portion forming a step with a top surface that is disposed closer to bottom surface 172 than the top surface of the proximal portion. The width of the distal portion may be less than that of the proximal portion, for example, to reduce the amount of physical contact between sample holder 102 and support pad 182. On such support pads, sample holder 102 sits on the distal step portion of support pad 182 and may either touch a side wall of the proximal pad portion or have a gap between it and the proximal pad portion. In the later case, tool may be used to laterally displace some of the material of the proximal pad portion to provide a holding force between the proximal pad portion and sample holder 102. Additionally or alternatively, sample holder 102 may be placed on support pads 182 that are configured to only contact the bottom side of sample holder 102, for example, to help reduce or prevent bending or bulking of the front and back faces of sample holder 102 (i.e., the faces into which through-holes 154 are located). In certain embodiments, an adhesive may be used on some or all the support pads 182 to secure sample holder 102 to base 164. In yet other embodiments, a downward force on the upper face of sample holder 102 is used to secure sample holder 102 to base 164, for example, at downward force on the sample holder 102 in the vicinity of at least some of the support pads 182. For example, a downward force may be applied to a peripheral portion of sample holder 102 by cover 170 when attached at element 520 of method 500. The downward force may be applied directly to sample holder 102 or through an intermediate spacer, seal, or gasket that is located on top of sample holder 102, for example, locate over a peripheral portion of sample holder 102. In some embodiments, samples are loaded into at least some of through-holes 154 prior to locating the sample holder 102 on or within base 164.

Regarding element 515 of method 500, biological samples may be loaded into one or more of through-holes 154 using one or more conventional pipettes. Alternatively, a custom loader may be used, for example, a loader comprising a plurality of pipette tips that allow more than one of through-holes 154 to be loaded simultaneously. In certain embodiments, the loader may comprises the loader disclosed in U.S. patent application Ser. No. 13/170,563, which is herein incorporated by reference in its entirety as if fully set forth herein. The biological samples may include one or more nucleotide sequences, amino acid sequences, or other biological macromolecules including, but not limited to, oligonucleotides, genes, DNA sequences, RNA sequences, polypeptides, proteins, enzymes, or the like. In addition, biological samples may include other molecules for controlling or monitoring a biological reaction including, but not limited to, primers, hybridization probes, reporter probes, quencher molecules, molecular beacons, fluorescent dyes, chemical buffers, enzymes, detergents, or the like. Additionally or alternatively, biological samples may include one or more genomes, cells, cellular nucleuses, or the like.

Regarding element 520 of method 500, cover 170 may be attached to base 164 about a peripheral region of base 164, for example, along top surface 168 of base 164. An adhesive may be used to attach cover 170 directly to base 164. Alternatively, gasket 171 may be used to attach cover 170, where an adhesive has been applied to top and bottom surface of gasket 171 and/or to portions of mating surfaces on base 164 and/or cover 170. The adhesive may be applied by a user just prior to attachment of cover 170 or may be applied during fabrication of cover 170, base 164, and/or gasket 171. In certain embodiments, a removable non-stick layer is applied on top of an adhesive layer that is removed prior to attachment of cover 170, for example, removable non-stick layer 194 shown in FIGS. 3, 9, and 10 over seal 171.

Regarding elements 525, 530, and 535 of method 500, a pipette, needle, or similar filling device may be inserted into fill port 178. A tip of the filling device inserted into the vicinity of indentation 180 in bottom surface 172 of base 164, for example, so that liquid may enter from into indentation 180 and air leave through insertion port 178 behind the filling device tip. Alternatively, a separate vent port may be provided in base 164 or cover 170 to allow air in cavity 176 of case 150 to leave from a different or addition location from fill port 178. In such embodiment, the filling device may be configured to form a seal with insertion port 178. Once cavity 176 has been filled or nearly filled with sealing fluid or liquid, the filling device may be removed or extracted from fill port 178, after which fill port 178 and/or any existing vent port may plugged or sealed in order to isolate the filled cavity 176 from the outside environment and/or to prevent or impede air from entering, or liquid from leaving, cavity 176. Fill port may be sealed using plug assembly 300, as described above herein. Alternatively, any type of plug or seal known in the art may be used. In certain embodiments, fill port 178, includes a valve that allows the filling device to be inserted during filling and then automatically closes as seals fill port 178 upon extraction of the filling device. In addition, if any separate vent ports are incorporated, these also may have a valve, such as a check valve, to maintain a closed cavity 176 after filling. In some embodiments, fill port 178 comprises a self-healing diaphragm that may be punctured by the filling device (e.g., a syringe needle) and then remain sealed upon removal of the filling device.

Regarding elements 540 and 545 of method 500, instrument 100 is configured to receive case 150—which includes sample holder 102 and its biological samples. In certain embodiments, one or more cases 150 are mounted on or in carrier 104, after which carrier 104 is received by instrument 100, along with the one or more cases 150. Instrument 100 is then used to perform one or more biological processes or experiments on the biological samples contained within through-holes 154. Instrument 100 may be configured to a qPCR, dPCR, end-point PCR, sequencing, genotyping, or other such procedure on one or more of the samples contained in through-holes 154 of sample holder 102. In certain embodiments, one or more sample holders 102 and/or cases 150 may be processed simultaneously by instrument 100 or associated optical system 106. As discussed above herein, one or more cases 150 may be mounted or attached to carrier 104, which is then received by instrument 100. In addition, instrument 100 may be configured to also receive other types of sample formats including, but not limited to, microtiter plates containing 48 sample wells, 96 sample wells, and 384 sample wells.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

The following list of co-pending U.S. applications are herein incorporated by reference in their entirely as if fully set forth herein:

U.S. Provisional Patent Application No. 61/541,453, filed on Sep. 30, 2011.
U.S. Provisional Patent Application No. 61/541,515, filed on Sep. 30, 2011.
U.S. Provisional Patent Application No. 61/541,342, filed on Sep. 30, 2011.
U.S. Design patent application Ser. No. 29/403,059, filed on Sep. 30, 2011.
U.S. Design patent application Ser. No. 29/403,049, filed on Sep. 30, 2011.
U.S. Provisional Patent Application No. 61/541,495, filed on Sep. 30, 2011.
U.S. Provisional Patent Application No. 61/541,366, filed on Sep. 30, 2011.
U.S. Provisional Patent Application No. 61/541,371, filed on Sep. 30, 2011.
U.S. Provisional Patent Application No. 61/564,027, filed on Nov. 28, 2011.
U.S. Provisional Patent Application No. 61/660,343, filed Jun. 15, 2012.

What is claimed is:

1. A case for containing a plurality of biological samples, the case comprising:
   a base comprising a bottom surface and plurality of side walls, the bottom surface and walls forming a cavity having a top opening;
   a fill port disposed within the base and configured to provide a port into the cavity;
   a substrate disposed inside the cavity and comprising a plurality of reaction regions configured to receive one or more biological samples, the substrate configured to be received into the cavity through the top opening; and
   a plug assembly comprising a plug and a plug driver, the plug comprising a distal end, the plug driver attached to the plug by an adhesive, a solder joint, or a weld joint;
   wherein the plug driver is configured to screw the distal end of the plug into the fill port using a first force or torque and to fracture or break the adhesive, solder joint, or weld joint using a second force or torque that is higher than the first force or torque.

2. The case of claim 1, wherein the substrate comprises a first surface and an opposing second surface, and the plurality of reaction regions comprises a plurality of through-holes disposed between the surfaces.

3. The case of claim 2, further comprising a cover having an inner surface, the inner surface having a central portion disposed over the plurality of reaction regions and a recessed portion surrounding the central portion.

4. The case of claim 1, wherein the reaction regions are through-holes.

5. A system for analyzing biological samples, the system comprising:
   the case of claim 1; and
   a thermal controller configured to maintain and/or cycle a temperature environment of the biological samples.

6. The system of claim 5, further comprising:
   an excitation source for illuminating the case; and
   an optical sensor for sensing fluorescent signals.

7. A system for analyzing a plurality of biological samples comprising:
   a case comprising:
     a base comprising a bottom surface and one or more side walls, the bottom surface and walls forming a cavity having a top opening;
     a fill port disposed in the base and configured to provide access to the cavity;
     a substrate disposed inside the cavity and comprising a plurality of reaction regions configured to receive one or more biological samples; and
     a cover configured to cover the top opening; and
   a plug assembly, the plug assembly comprising:
     a plug configured to be received in the fill port so as to fluidically seal the fill port, and
     a plug driver configured to be removably attached to the plug by an adhesive, a solder joint, or a weld joint and configured to screw the plug into the fill port.

8. The system of claim 7, wherein the plug driver is configured to separate from the plug in response to a torque applied to the plug driver meeting a threshold.

9. The system of claim 7, further comprising:
a thermal controller configured to maintain and/or cycle a temperature environment of the biological samples;
an excitation source for illuminating the case; and
an optical sensor for sensing fluorescent signals.

10. The system of claim 7, wherein the cover of the case has an inner surface including a central portion disposed over the plurality of reaction regions and a recessed portion surrounding the central portion.

11. The system of claim 10, wherein the central portion has contours configured to direct air bubbles away from the central portion to the recessed portion.

12. A method comprising:
providing a case comprising:
a base comprising a bottom surface and plurality of side walls, the bottom surface and walls forming a cavity having a top opening;
a fill port disposed within the base and configured to provide a port into the cavity;
a substrate disposed inside the cavity and comprising a plurality of reaction regions configured to receive one or more biological samples, the substrate configured to be received into the cavity through the top opening; and
a plug assembly comprising a plug and a plug driver, the plug comprising a distal end, the plug driver attached to the plug by an adhesive, a solder joint, or a weld joint;
wherein the plug driver is configured to screw the distal end of the plug into the fill port using a first force or torque and to fracture or break the adhesive, solder joint, or weld joint using a second force or torque that is higher than the first force or torque;
loading one or more biological samples into at least some of the reaction regions;
enclosing the substrate within the cavity by locating a cover over base;
filling the cavity with a fluid via the fill port;
attaching the plug assembly to the fill port by applying the first force or torque; and
applying the second force or torque to fracture or break the adhesive, solder joint, or weld joint.

13. The method of claim 12, further comprising:
mounting the base, the substrate, and the cover into an instrument; and
operating the instrument to monitor a biological reaction in one or more through-holes of the substrate.

14. The method of claim 12, wherein the substrate comprises a first surface and an opposing second surface, and the plurality of reaction regions comprises a plurality of through-holes disposed between the surfaces, the through-holes configured to receive one or more biological samples.

15. The method of claim 12, wherein the cover comprises an inner surface in contact with the fluid, the inner surface including a central portion disposed over a plurality of through-holes disposed in the substrate and a recessed portion surrounding the central portion.

16. The method of claim 15, further comprising introducing a gas into the cavity, wherein the gas is substantially confined within the recessed portion.

17. The method of claim 16, wherein the gas comprises a plurality of air bubbles.

18. The method of claim 16, wherein introducing a gas into the cavity occurs simultaneously with filling the cavity.

* * * * *